(12) United States Patent
Fukuyama (10) Patent No.: US 11,096,572 B2
(45) Date of Patent: Aug. 24, 2021

(54) SCANNING OPTICAL SYSTEM AND OBSERVATION APPARATUS

(71) Applicant: Olympus Corporation, Hachioji (JP)

(72) Inventor: Hiroya Fukuyama, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 210 days.

(21) Appl. No.: 16/219,162

(22) Filed: Dec. 13, 2018

(65) Prior Publication Data

US 2019/0110680 A1 Apr. 18, 2019

Related U.S. Application Data (63) Continuation of application No. PCT/JP2016/067706, filed on Jun. 14, 2016.

(51) Int. Cl.
*A61B 3/10* (2006.01)
*G02B 13/08* (2006.01)
(Continued)

(52) U.S. Cl.
CPC .............. *A61B 3/1025* (2013.01); *G02B 7/04* (2013.01); *G02B 9/60* (2013.01); *G02B 13/08* (2013.01);
(Continued)

(58) Field of Classification Search
CPC .... A61B 3/1025; G02B 13/08; G02B 26/101; G02B 7/04; G02B 9/60; G02B 26/105
See application file for complete search history.

(56) References Cited

U.S. PATENT DOCUMENTS

2004/0008248 A1 1/2004 Iima et al.
2012/0134000 A1 5/2012 Kusaka et al.
(Continued)

FOREIGN PATENT DOCUMENTS

JP 11-326816 11/1999
JP 11-326817 11/1999
(Continued)

OTHER PUBLICATIONS

International Search Report and Written Opinion from corresponding International Application No. PCT/JP2016/067706, dated Aug. 9, 2016.

*Primary Examiner* — Kimberly N. Kakalec
(74) *Attorney, Agent, or Firm* — Scully, Scott, Murphy & Presser, P.C.

(57) ABSTRACT

The disclosed technology is directed to placing two galvanometer mirrors in a pupil conjugate relationship and at the same time preventing astigmatism from occurring while preventing images from being degraded by flaws and foreign matter on a lens. A scanning optical system includes two one-dimensional scanning means disposed closely to each other at a spaced interval therebetween in an optical axis direction for scanning a light beam from a light source in two scanning directions. An objective lens for focusing the light beam scanned by the scanning means onto a target. A plurality of optical elements is disposed in positions spaced from an intermediate image plane in the optical axis direction and having different optical powers in the two scanning directions. The positions and the optical powers of the respective optical elements are set to compensate for the spaced interval between the two scanning means in the optical axis direction.

6 Claims, 10 Drawing Sheets

(51) Int. Cl.
  *G02B 26/10* (2006.01)
  *G02B 7/04* (2021.01)
  *G02B 9/60* (2006.01)
(52) U.S. Cl.
  CPC ......... *G02B 26/101* (2013.01); *G02B 26/105* (2013.01)

(56) References Cited

U.S. PATENT DOCUMENTS

| | | |
|---|---|---|
| 2013/0021576 A1 | 1/2013 | Saito |
| 2016/0025970 A1 | 1/2016 | Fukuyama |

FOREIGN PATENT DOCUMENTS

| | | |
|---|---|---|
| JP | 2003-315726 | 11/2003 |
| JP | 2004-070312 | 3/2004 |
| JP | 2008-181070 | 8/2008 |
| JP | 4817356 | 9/2011 |
| JP | 2011-224037 | 11/2011 |
| JP | 2011-232661 | 11/2011 |
| JP | 2012-145687 | 8/2012 |
| JP | 2013-142768 | 7/2013 |
| JP | 2014-108212 | 6/2014 |
| WO | 2014163114 | 10/2014 |

SCANNING OPTICAL SYSTEM AND OBSERVATION APPARATUS

CROSS-REFERENCE TO RELATED APPLICATION

This application is a continuation application of PCT Application No. PCT/JP 2016/067706 filed on Jun. 14, 2016, which is hereby incorporated by reference in its entirety.

TECHNICAL FIELD

The technology disclosed herein generally relates to a scanning optical system and an observation apparatus.

DESCRIPTION OF THE RELATED ART

There is known a scanning optical system having so-called proximity galvanometer mirrors for scanning a light beam in two scanning directions with two one-dimensional galvanometer mirrors that are disposed in close proximity to each other along an optical axis as disclosed in Unexamined Japanese Patent Application Publication No. 2011-224037. The scanning optical system includes a lens having different powers in the scanning directions, disposed at an intermediate image plane, thereby placing the two galvanometer mirrors in a pupil conjugate relationship.

The scanning optical system disclosed in Japanese Patent JP 2011-224037 is disadvantageous in that since the lens having different powers in the scanning directions is disposed at the intermediate image plane, flaws and foreign matter on the lens produce noise images. If the lens is disposed at a position spaced from the intermediate image plane, then noise images from flaws and foreign matter are removed, but astigmatism occurs.

BRIEF SUMMARY OF EMBODIMENTS

The disclosed technology is directed to a scanning optical system and an observation apparatus which place two galvanometer mirrors in a pupil conjugate relationship and at the same time prevent astigmatism from occurring while preventing images from being degraded by flaws and foreign matter on a lens.

According to an aspect of the present disclosure, there is provided a scanning optical system including two one-dimensional scanning means disposed closely to each other at a spaced interval therebetween in an optical axis direction for scanning a light beam from a light source in two scanning directions. An objective lens focuses the light beam scanned by the scanning means onto a target. A plurality of optical elements are disposed in positions spaced from an intermediate image plane in the optical axis direction and have different optical powers in the two scanning directions. The positions and the optical powers of the respective optical elements are set to compensate for the spaced interval between the two scanning means in the optical axis direction.

According to the present aspect, so-called anamorphic optical elements having different optical powers in the two scanning directions adjust a pupil focusing relationship so as to compensate for the distance between the two scanning means in the optical axis direction, simultaneously placing the two scanning means that are shifted from each other in the optical directions in positions that are optically conjugate to the pupil plane of the objective lens. In this case, placing the anamorphic optical elements in a spaced relationship from the intermediate image plane acts equivalently to placing a single anamorphic optical element having a combined optical power on the intermediate image plane.

In other words, the anamorphic optical elements that are spaced from the intermediate image plane in the optical axis direction are prevented from producing noise from flaws and foreign matter on surfaces of the anamorphic optical elements. The anamorphic optical elements that are equivalently placed on the intermediate image plane are capable of restraining the occurrence of astigmatism.

In the above aspect, the optical elements may be disposed at a spaced interval therebetween across the intermediate image plane in the optical axis direction, and the optical elements may have different combined optical powers in the two scanning directions.

With this arrangement, since the optical elements disposed at a spaced interval from each other across the intermediate image plane in the optical axis direction have different optical powers in the scanning directions, a combined optical power thereof is equivalent to the optical power of a single optical element disposed between two optical elements. In other words, though the two optical elements are disposed in respective positions spaced from the intermediate image plane, they act equivalently to a single anamorphic optical element placed on the intermediate image plane. Both of the two scanning means can thus be disposed in respective positions that are optically conjugate to the pupil plane of the objective lens without producing astigmatism. As the two optical elements are disposed in positions spaced from the intermediate image plane, it is possible to prevent noise from being produced by flaws and foreign matter on the optical elements.

In the above aspect, the plurality of optical elements is defined as two optical elements disposed on one side of the intermediate image plane at a spaced interval therebetween in the optical axis direction, and one of the plurality of optical elements that is closer to the intermediate image plane and another one of the plurality of optical elements that is farther from the intermediate image plane may have respective optical powers of different signs.

With this arrangement, the two optical elements make up a retrofocus lens system, thereby functioning equivalently to a single anamorphic optical element disposed outside of the two optical elements.

In other words, by placing the two optical elements such that an equivalent single anamorphic optical element is positioned on the intermediate image plane, the two scanning means are disposed in a state conjugate to the pupil plane of the objective lens without causing astigmatism. Furthermore, because the two optical elements are spaced from the intermediate image plane, noise is prevented from being produced by flaws and foreign matter on the optical elements.

In the above aspect, the optical elements may make up an afocal optical system and may be disposed between the scanning means and a pupil plane of the objective lens.

With this arrangement, the afocal optical system can focus an image point corresponding to an object point at a finite distance by moving in the optical axis direction to an extent according to conditions. Using this property, the two scanning means that are spaced from each other in the optical axis direction can be disposed in a state optically conjugate to the pupil plane of the objective lens.

In other words, by placing a plurality of anamorphic optical elements making up a Galileo-type afocal system in close proximity of the pupil plane of the objective lens or the scanning means, it is possible to bring a pupil position corresponding to either one of the scanning directions closer to or farther from a pupil position corresponding to the other scanning direction. Moreover, since the afocal optical system is largely spaced from the intermediate plane, it is possible to prevent noise from being produced by flaws and foreign matter on the anamorphic optical elements.

In the above aspect, the optical elements may include a first optical element portion disposed between the scanning means and a pupil plane of the objective lens and a second optical element portion disposed in a position that is optically conjugate to the first optical element portion, having a property optically complementary to the first optical element portion, and canceling out an optical power of the first optical element portion in an entire optical system.

With this arrangement, the first optical element portion which includes anamorphic optical elements places both of the two scanning means with a spaced interval therebetween in the optical axis direction in a state that is optically conjugate to the pupil plane of the objective lens. The second optical element portion which includes anamorphic optical elements cancels out astigmatism caused by having the first optical element portion spaced from the intermediate image plane, in the entire optical system.

It is thus possible to prevent noise from being produced by flows and foreign matter on the first optical element portion and the second optical element portion.

In particular, if the anamorphic optical elements are largely spaced from the intermediate image plane, then large astigmatism occurs between the two anamorphic optical elements. Consequently, even though another optical element between the two anamorphic optical elements and the intermediate image plane are positioned in close proximity to each other, since the intermediate image plane itself has astigmatism, noise is prevented from being produced by flaws and foreign matter on the other optical element. As a result, even when an internal focusing lens largely moves the intermediate image plane, no image is clearly focused on the other optical element due to astigmatism, preventing the intermediate image plane from being aligned, so that noise is prevented from being produced by flaws and foreign matter.

In the above aspect, the first optical element portion may include two optical elements disposed closely to the pupil plane of the objective lens at a spaced interval therebetween in the optical axis direction, and the optical element that is closer to the pupil plane and the optical element that is farther from the pupil plane may have respective optical powers of different signs.

With this arrangement, the first optical element portion may make up a retrofocus optical system, increasing the distance between principal points to make the pupil plane of the objective lens and the two scanning means optically conjugate to each other. If both the first optical element portion and the second optical element portion make up retrofocus optical systems, then the elements from the light source to the objective lens can be placed fully in a pupil conjugate relationship.

In the above aspect, the first optical element portion may include two first optical elements, one of the first optical elements being disposed closely to the pupil plane of the objective lens and other first optical element being disposed at a spaced interval from the pupil plane of the objective lens in the optical axis direction, and the second optical element portion may include two second optical elements, the second optical elements being disposed in respective positions that are optically conjugate to the first optical elements of the first optical element portion and having respective properties that are optically complementary to each other.

According to another aspect of the present disclosure, there is provided an observation apparatus having either one of the scanning optical systems described hereinbefore.

In the above aspect, the observation apparatus may include an internal focusing lens.

The present disclosure is advantageous in that two galvanometer mirrors are placed in a pupil conjugate relationship and at the same time astigmatism is prevented from occurring while preventing images from being degraded by flaws and foreign matter on a lens.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The observation apparatus according to the present embodiment includes the scanning optical system 1 that converges a light beam from a light source onto a subject or target O and scans two-dimensionally the subject O with the light beam.

Figure 1:
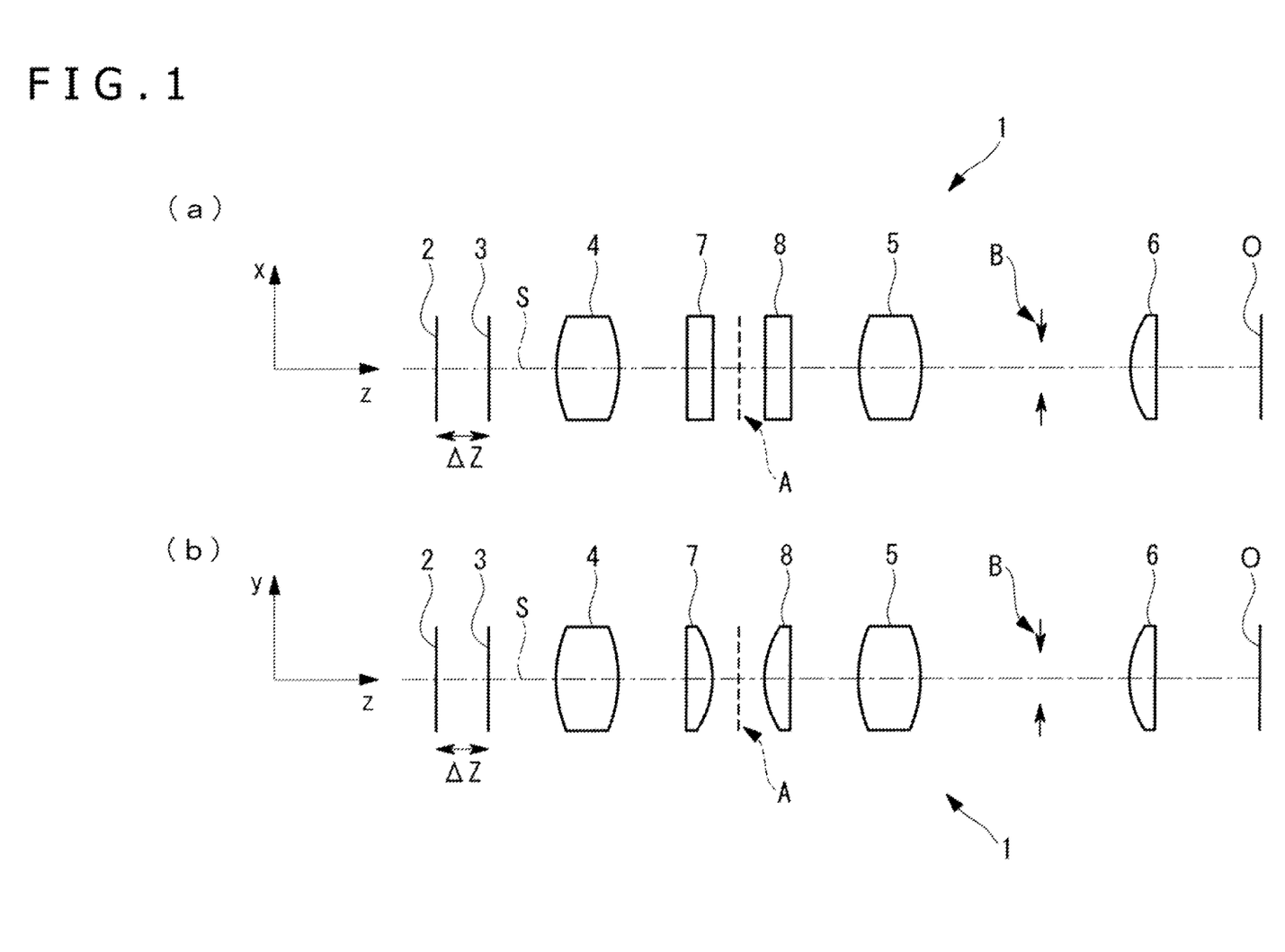
FIG. 1 is a schematic diagram of a scanning optical system according to a first embodiment of the disclosed technology, illustrating a vertical cross-sectional shape thereof in (a) xz directions and in (b) yz directions.

As illustrated in FIG. 1(a) and FIG. 1(b), the scanning optical system 1 according to the present embodiment includes two one-dimensional galvanometer mirrors or scanning means 2 and 3 disposed in close proximity to each other at a spaced interval therebetween in an optical axis S direction, for scanning a light beam from a light source in two scanning directions or x and y directions, relay lenses 4 and 5 for relaying the light beams scanned by the galvanometer mirrors 2 and 3 while forming an intermediate image, an objective lens 6 for converging the light beam relayed by the relay lenses 4 and 5 onto a subject O, and two cylindrical lenses or optical elements 7 and 8 as anamorphic optical elements disposed at positions spaced from an intermediate image plane A in optical axis S directions and having different optical powers in the two scanning directions. The two one-dimensional galvanometer mirrors or scanning means 2 and 3 are also defined by respective first and second one-dimensional scanners.

The galvanometer mirror 2 for scanning the light beam in the x direction is disposed in a position that is optically conjugate to a pupil plane B of the objective lens 6, as illustrated in FIG. 1(a). On the other hand, the galvanometer mirror 3 for scanning the light beam in the y direction is disposed in a position closer to the pupil plane B of the objective lens 6 than the galvanometer mirror 2 by a distance Δz, as illustrated in FIG. 1(b).

Each of the cylindrical lenses 7 and 8 has an optical power of zero in the x direction and a positive optical power in the y direction which has a magnitude capable of compensating for the distance Δz between the two galvanometer mirrors 2 and 3. In other words, the optical power component in the y direction has a positive combined optical power larger than in the x direction, which is able to achieve a positional relationship that is optically conjugate to the pupil plane B of the objective lens 6 at a shorter distance than in the x direction.

In the scanning optical system 1 according to the present embodiment, the two cylindrical lenses 7 and 8 are disposed in positions on both sides of the intermediate image plane A and spaced from each other in the optical axis S directions. Each of the cylindrical lenses 7 and 8 is thus disposed in a position spaced from the intermediate image plane A along the optical axis S.

Operation of the scanning optical system 1 is arranged as described hereinbefore according to the present embodiment and will be described hereinafter.

With the scanning optical system 1 according to the present embodiment, a light beam emitted from the light source is scanned in the x direction by the x-direction galvanometer mirror 2, and then scanned in the y direction by the y-direction galvanometer mirror 3. The two galvanometer mirrors 2 and 3 can thus direct the light beam in any arbitrary direction of the two-dimensional directions transverse to the optical axis S.

The light beam scanned by the two galvanometer mirrors 2 and 3 is converged by the first relay lens 4, focused onto the intermediate image plane A, converted into substantially parallel light by the second relay lens 5, applied to the objective lens 6, and converged onto each position on the subject O by the objective lens 6.

Since the x-direction galvanometer mirror 2 is disposed in the position that is optically conjugate to the pupil plane B of the objective lens 6, and the two relay lenses 4 and 5 are disposed in a so-called 4f optical system, principal rays of the light beam lie parallel to the optical axis S between the two relay lenses 4 and 5 in the x direction. Since the two cylindrical lenses 7 and 8 disposed on both sides of the intermediate image plane A have no optical power in the x direction, the light beam is not converged in the x direction, and is transmitted through the two cylindrical lenses 7 and 8 while the principal rays remain parallel to the optical axis S. The light beam that is emitted from the second relay lens 5 becomes substantially parallel light and has its principal rays crossing the optical axis S at the pupil plane B of the objective lens 6.

On the other hand, since the y-direction galvanometer mirror 3 is disposed off the position that is optically conjugate to the pupil plane B of the objective lens 6 in the case where no power of the cylindrical lenses 7 and 8 is taken into consideration, toward the objective lens 6 by the distance Δz, the light beam has its principal rays inclined to the optical axis S at the time when it passes through the first relay lens 4. As the two cylindrical lenses 7 and 8 have an optical power in the y direction, the light beam is converged in the y direction, and has its principal rays lying parallel to the optical axis S at the time when it passes through the two cylindrical lenses 7 and 8. The light beam that is emitted from the second relay lens 5 becomes substantially parallel light in the y direction, as in the x direction, and has its principal rays crossing the optical axis S at the pupil plane B of the objective lens 6.

The description given hereinafter applies where the cylindrical lenses 7, 8, etc. are not taken into consideration unless clearly specified, in discussing the conjugate relationship between the galvanometer mirrors 2, 3 and the pupil plane B of the objective lens 6.

Figure 2:
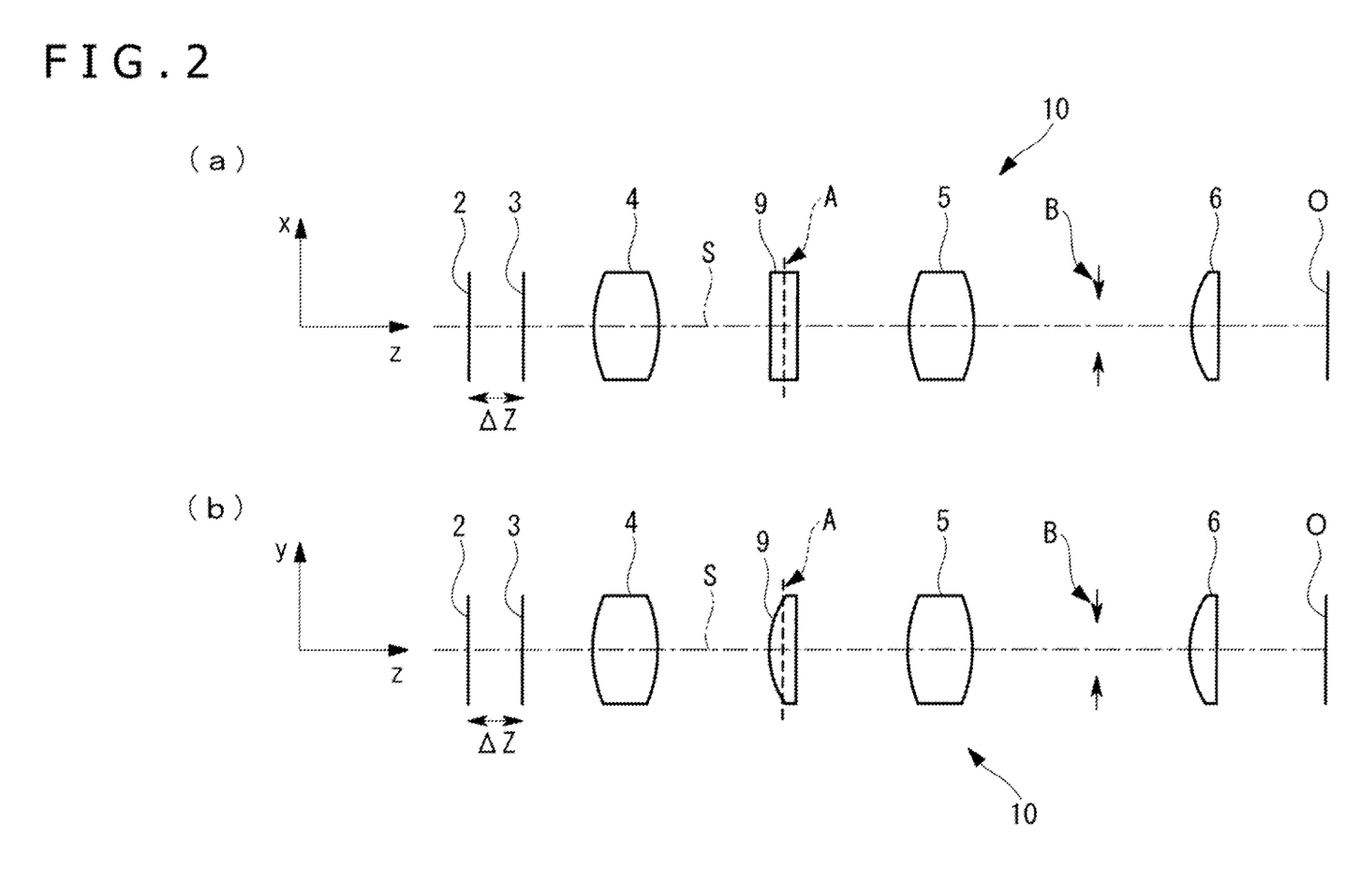
FIG. 2 is a schematic diagram of a conventional scanning optical system equivalent to the scanning optical system of FIG. 1, illustrating a vertical cross-sectional shape thereof in (a) xz directions and in (b) yz directions.

According to the present embodiment, specifically, since the two cylindrical lenses 7 and 8 are disposed in positions on both sides of the intermediate image plane A and spaced from each other in the optical axis S directions, the scanning optical system 1 is equivalent to a scanning optical system in which, as illustrated FIGS. 2(a) and 2(b), a single cylindrical lens 9 having the same optical power as the combined optical power of the two cylindrical lenses 7 and 8 is disposed in a position aligned with the intermediate image plane A.

As a result, according to the present embodiment, the combined optical power of the two cylindrical lenses 7 and 8 places not only the x-direction galvanometer mirror 2, but also the y-direction galvanometer mirror 3, in a positional relationship that is optically conjugate to the pupil plane B of the objective lens 6. Thus, the light beam is prevented from being vignetted at the pupil plane B of the objective lens 6, allowing light that is uniform in brightness in the peripheral field of vision to be applied the subject O. Inasmuch as the scanning optical system 1 is equivalent to the scanning optical system in which the single cylindrical lens 9 is disposed in the position aligned with the intermediate image plane A, as described hereinbefore, the scanning optical system 1 is able to prevent astigmatism from occurring.

Furthermore, as the scanning optical system 1 according to the present embodiment includes the cylindrical lenses 7 and 8 disposed in the positions spaced from the intermediate image plane A in the optical axis S directions, unlike the scanning optical system 10 illustrated in FIGS. 2(a) and 2(b), even if flaws and foreign matter are present on the cylindrical lenses 7 and 8, the scanning optical system 1 is advantageous in that it is able more reliably to prevent such flaws and foreign matter from being detected as noise.

According to the present embodiment, the optical power in the x direction of the cylindrical lenses 7 and 8 is set to zero because the galvanometer mirror 2 is disposed in a position that is optically conjugate to the pupil plane B of the objective lens 6. Alternatively, the galvanometer mirror 3 may be disposed in a position that is optically conjugate to the pupil plane B of the objective lens 6, the optical power in the x direction of the cylindrical lenses 7 and 8 may be set to a negative value, and the optical power in the y direction of the cylindrical lenses 7 and 8 may be set to zero.

Furthermore, there may be employed arbitrary anamorphic optical elements, in which both of the galvanometer mirrors 2 and 3 are displaced off the positions that are optically conjugate to the pupil plane B of the objective lens 6 and the optical powers in the scanning directions x and y are set to values other than zero.

The two cylindrical lenses 7 and 8 do not need to have the same optical power insofar as they have optical powers of the same sign.

A scanning optical system 11 according to a second embodiment of the present invention will be described hereinafter with reference to the drawings.

Those parts of the present embodiment which share common structures with those of the scanning optical system 1 according to the first embodiment described hereinbefore are denoted by identical reference characters and will not be described hereinafter.

Figure 3:
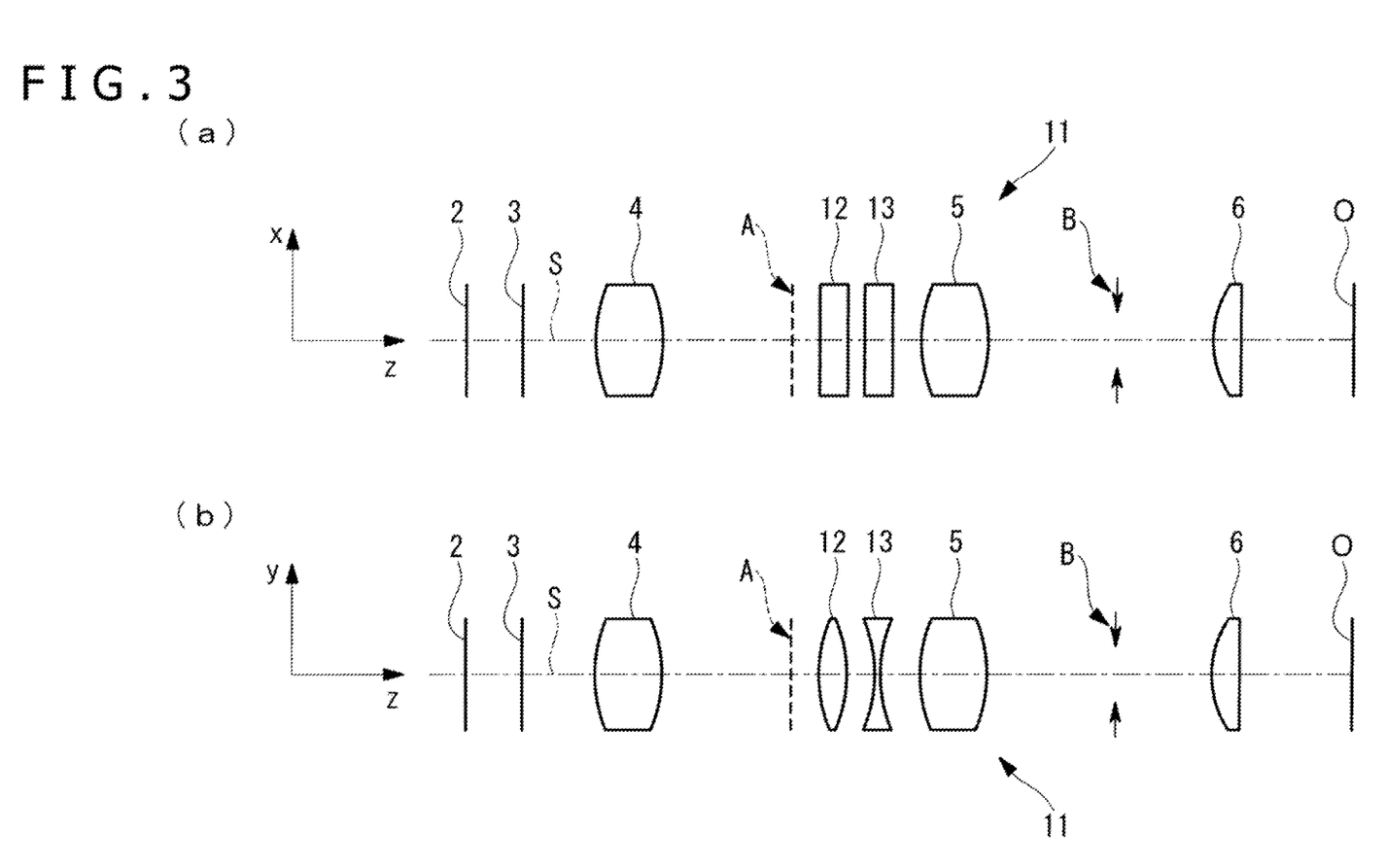
FIG. 3 is a schematic diagram of a scanning optical system according to a second embodiment of the present invention, illustrating a vertical cross-sectional shape thereof in (a) xz directions and in (b) yz directions.

As illustrated FIGS. 3(a) and 3(b), the scanning optical system 11 according to the present embodiment is different from the scanning optical system 1 according to the first embodiment as to the layout and structures of cylindrical lenses 12 and 13.

In the scanning optical system 1 according to the first embodiment, the two cylindrical lenses 7 and 8 having optical powers of the same sign in the y direction are disposed in positions on both sides of the intermediate image plane A at a spaced interval along the optical axis. However, as illustrated FIG. 3(b), the scanning optical system 11 is different from the scanning optical system 1 according to the first embodiment in that the two cylindrical lenses or optical elements 12 and 13 whose vertical cross-sectional shapes in the y direction are double convex and double concave, respectively, are juxtaposed in the optical axis S directions.

One of the cylindrical lenses 12 whose vertical cross-sectional shape in the y direction is double convex and has a positive optical power is of a vertical cross-sectional shape in the x direction that represents a parallel flat plate and has no optical power. The other cylindrical lens 13 whose vertical cross-sectional shape in the y direction is double concave and has a negative optical power is also of a vertical cross-sectional shape in the x direction that represents a parallel flat plate and has no optical power.

The cylindrical lens 13 whose vertical cross-sectional shape in the y direction represents a double-concave lens is disposed in a position more spaced from the intermediate image plane A than the cylindrical lens 12 whose vertical cross-sectional shape in the y direction represents a double-convex lens. These lenses thus make up a retrofocus lens system. The retrofocus lens system made up of the two cylindrical lenses 12 and 13 combined together functions equivalently to a lens system, in which a single cylindrical lens is disposed outside of the two cylindrical lenses 12 and 13.

Specifically, the positions and optical powers of the two cylindrical lenses 12 and 13 may be adjusted to provide a retrofocus lens system that is equivalent to a lens system, in which a single cylindrical lens as a anamorphic optical element is disposed in a position aligned with the intermediate image plane A.

As a result, both of the two galvanometer mirrors 2 and 3 are disposed in a positional relationship that is optically conjugate to the pupil plane B of the objective lens 6, so that the light beam is prevented from being vignetted at the pupil plane B of the objective lens 6, allowing light that is uniform in brightness in the peripheral field of vision to be applied the subject O. Inasmuch as the scanning optical system 11 is equivalent to the scanning optical system 10 illustrated FIG. 2, in which the single cylindrical lens 9 is disposed in the position aligned with the intermediate image plane A, the scanning optical system 10 is able to prevent astigmatism from occurring.

Furthermore, as the cylindrical lenses 12 and 13 are disposed in positions spaced from the intermediate image plane A in the optical axis S directions, even if flaws and foreign matter are present on the cylindrical lenses 12 and 13, the scanning optical system 11 is able more reliably to prevent such flaws and foreign matter from being detected as noise.

In the present embodiment, a combination of two cylindrical lenses 12 and 13 having a positive combined power in the y direction is used as a retrofocus lens system. However, a combination of two cylindrical lenses 12 and 13 having a negative combined power in the y direction may be used instead.

Figure 4:
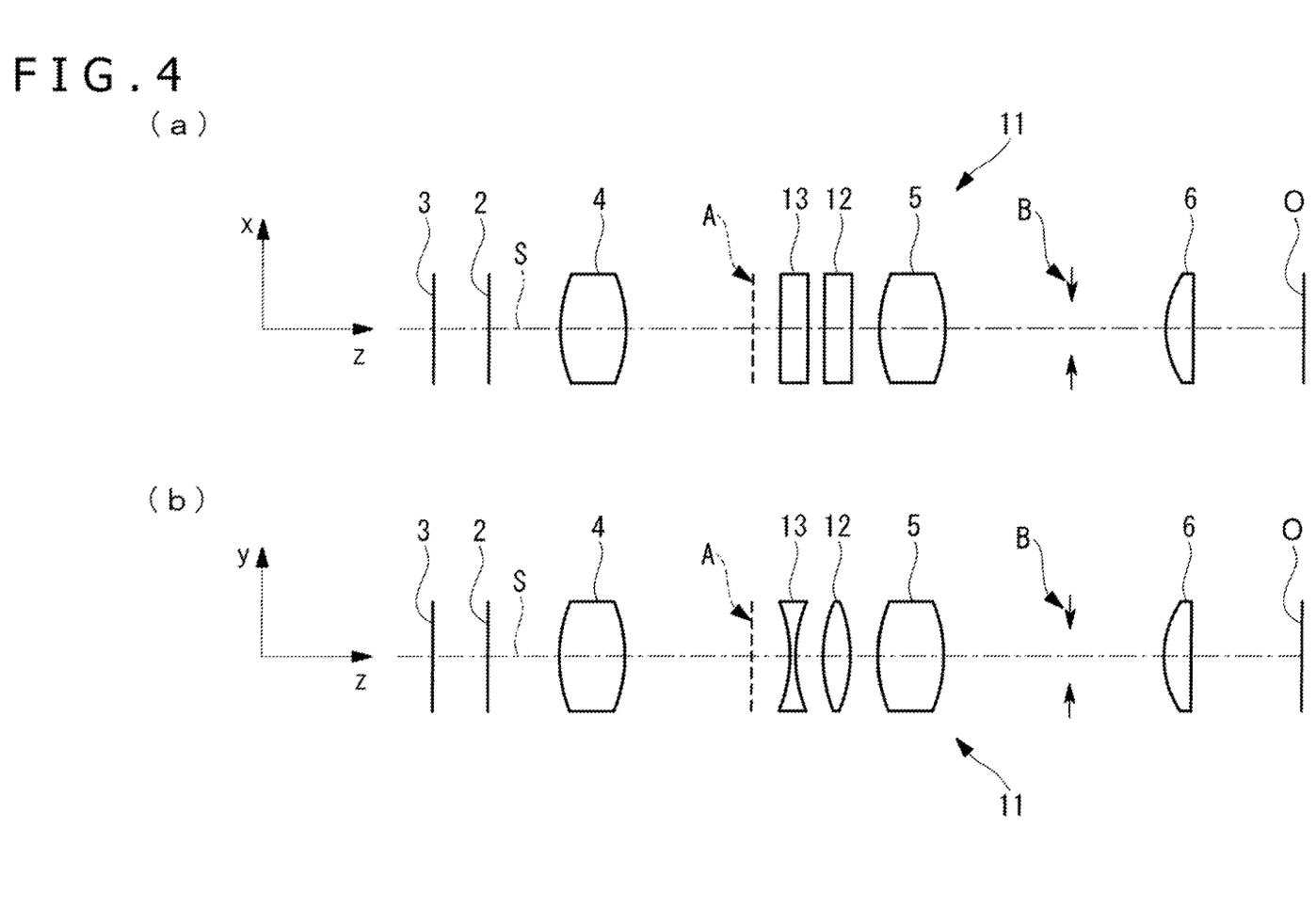
FIG. 4 is a schematic diagram of a modification of the scanning optical system of FIG. 3, illustrating a vertical cross-sectional shape thereof in (a) xz directions and in (b) yz directions.

In such a case, as illustrated FIGS. 4(a) and 4(b), in the x direction where there is no optical power, the x-direction galvanometer mirror 2 and the pupil plane B of the objective lens 6 are disposed in optically conjugate positions. In the y direction, the y-direction galvanometer mirror 3 that is more spaced from the pupil plane B than the x-direction galvanometer mirror 2 and the pupil plane B of the objective lens 6 are disposed in optically conjugate positions. The proximity galvanometer mirror 3 is disposed in the position that is conjugate to the pupil planes B. One of the proximity galvanometer mirrors 3 is moved toward the subject O, and the lens corresponding to the proximity galvanometer mirror 3 that is moved is also moved.

A scanning optical system 14 according to a third embodiment of the present disclosure will be described hereinafter with reference to the drawings.

Those parts of the present embodiment which share common structures with those of the scanning optical system 11 according to the second embodiment described hereinbefore are denoted by identical reference numerals and will not be described hereinafter.

Figure 5:
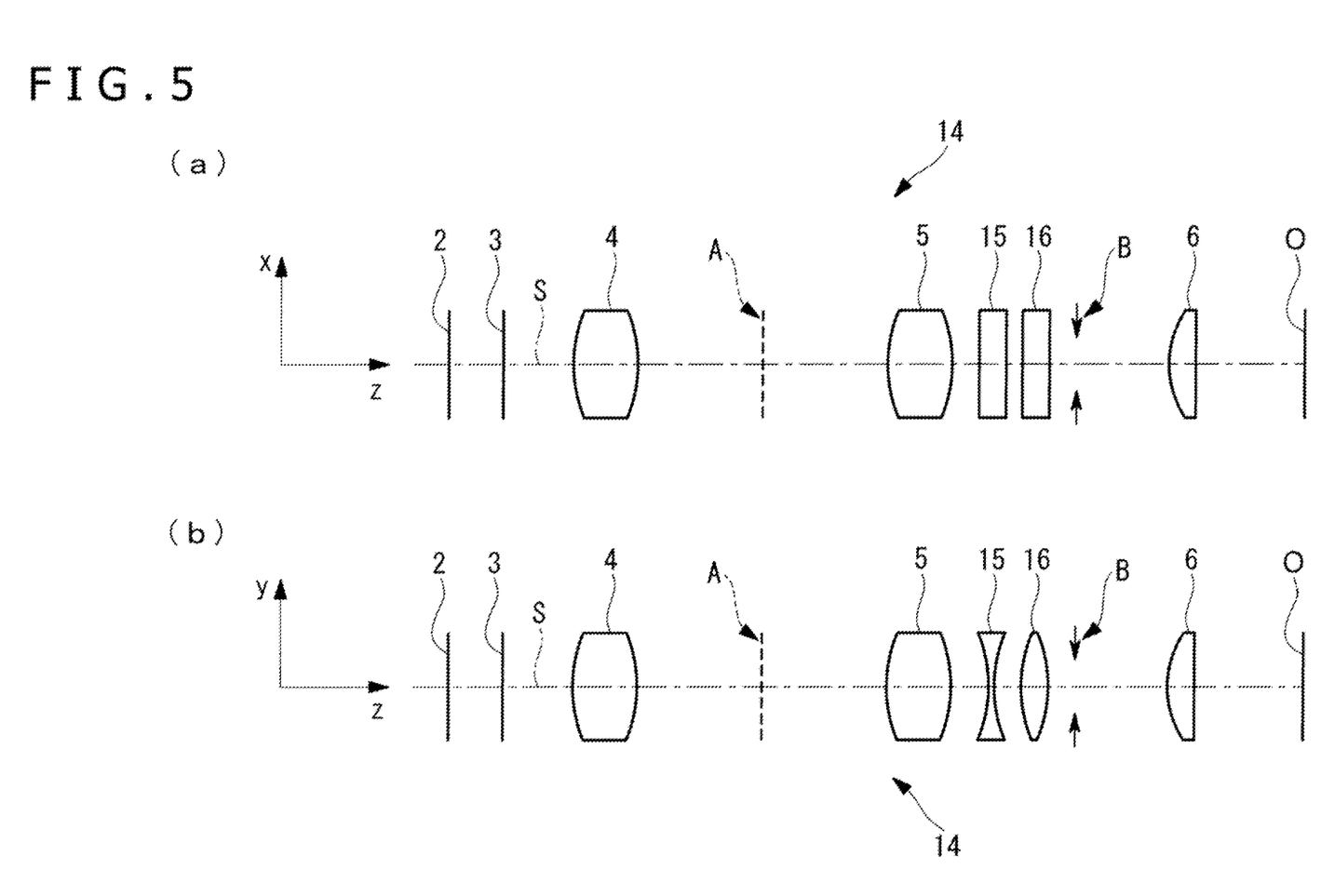
FIG. 5 is a schematic diagram of a scanning optical system according to a third embodiment of the present invention, illustrating a vertical cross-sectional shape thereof in (a) xz directions and in (b) yz directions.

As illustrated FIGS. 5(a) and 5(b), the scanning optical system 14 according to the present embodiment is different from the scanning optical system 11 according to the second embodiment as to the layout and structures of cylindrical lenses 15 and 16.

The scanning optical system 14 according to the present embodiment uses, as illustrated in FIG. 5(b), two types of cylindrical lenses 15 and 16 whose vertical cross-sectional shapes in the y direction are double convex and double concave, respectively, as with the second embodiment, but is different from the second embodiment in that the cylindrical lenses 15 and 16 are disposed in close proximity to the pupil plane B of the objective lens 6 and that the double-convex lens and the double-concave lens are arrayed successively from the pupil plane B, providing Galileo-type afocal system.

With this arrangement, using the property of the afocal system that it focuses an image point corresponding to an object point at a finite distance by moving in an optical axis S direction to an extent according to conditions, the pupil position of the objective lens 6 in the y direction as viewed from the galvanometer mirror 3 side is moved in the optical axis S direction to make the galvanometer mirror 3 optically conjugate to the pupil plane B of the objective lens 6. Since the lenses of the afocal system are spaced from the intermediate image plane A of the objective lens 6, noise is prevented from being produced from flaws and foreign matter on the lenses.

A scanning optical system 17 according to a fourth embodiment of the present disclosure will be described hereinafter with reference to the drawings.

Those parts of the present embodiment which share common structures with those of the scanning optical system 1 according to the first embodiment described hereinbefore are denoted by identical reference numerals and will not be described hereinafter.

Figure 6:
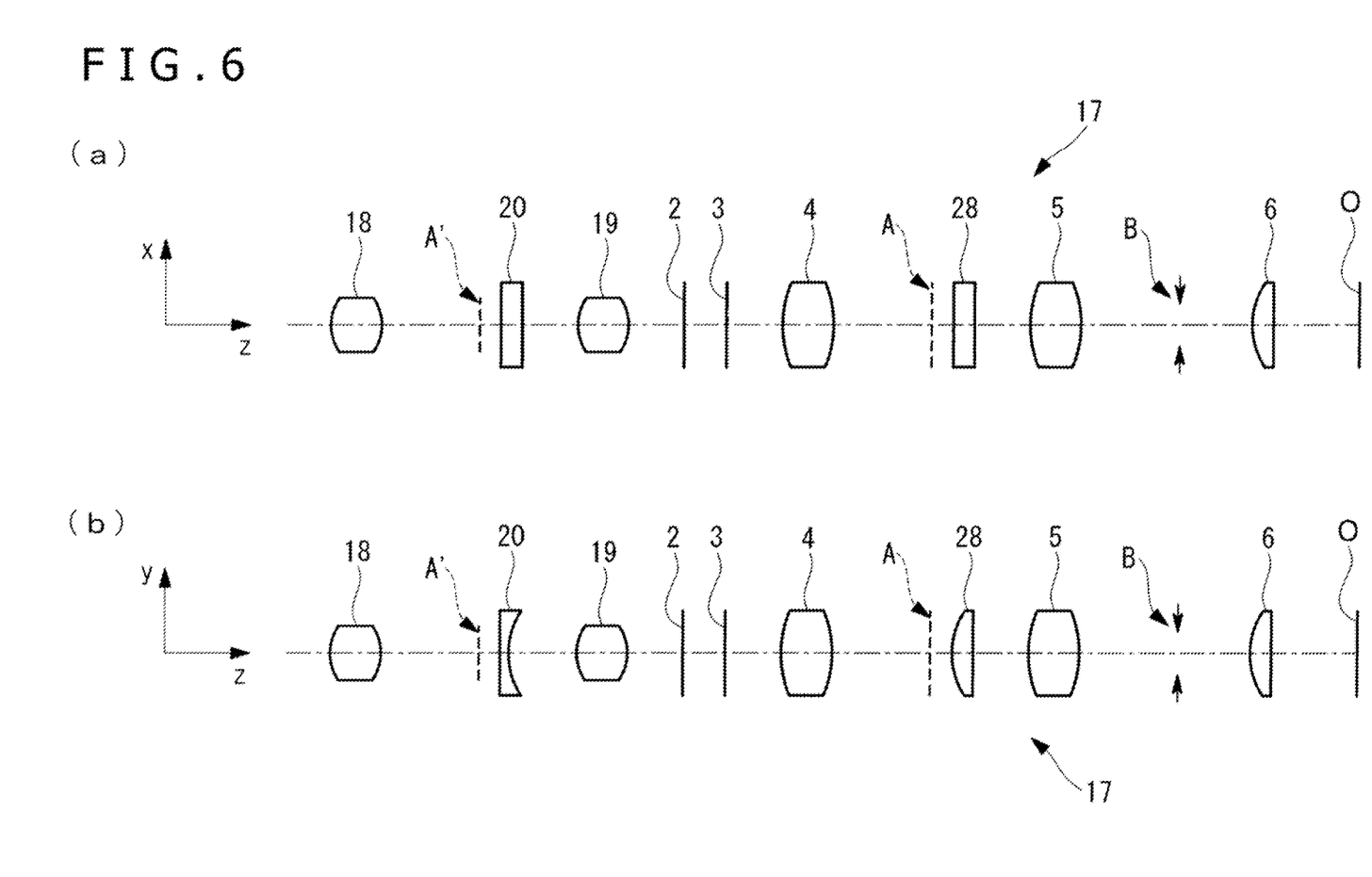
FIG. 6 is a schematic diagram of a scanning optical system according to a fourth embodiment of the present invention, illustrating a vertical cross-sectional shape thereof in (a) xz directions and in (b) yz directions.

As illustrated in FIGS. 6(a) and 6(b), the scanning optical system 17 according to the present embodiment is different from the scanning optical system 1 according to the first embodiment as to the layout and structure of a cylindrical lens 20.

According to the present embodiment, the scanning optical system 17 includes a plurality of relay lenses 18, 19 positioned more closely to the light source than the two galvanometer mirrors 2 and 3 and the intermediate image plane A and the pupil plane B are relayed by the relay lenses 4, 5, 18, and 19 to form optically conjugate positions A' and B'.

A single cylindrical lens or first optical element 28 that has the same power as the combined power of the cylindrical lenses 7 and 8 is disposed in place of one of the cylindrical lenses that is disposed in close proximity to the intermediate image plane A in the first embodiment, and another cylindrical lens or second optical element 20 that is complementary in shape to the cylindrical lens 28 is disposed in place of the other cylindrical lens 7 that is spaced from the cylindrical lens 8 in the optical axis S direction across the intermediate image plane A, in a position that is optically conjugate to the cylindrical lens 28 in close proximity to the position A' that is conjugate to the intermediate image plane A.

With the scanning optical system 17 thus arranged according to the present embodiment, one of the cylindrical lenses 28 disposed in close proximity to the intermediate image plane A compensates for a shift of the y-direction galvanometer mirror 3 in an optical axis S direction, placing the galvanometer mirror 3 in a position that is optically conjugate to the pupil plane B of the objective lens 6. The other complementary cylindrical lens 20 is disposed in a position that is optically conjugate to the cylindrical lens 28, canceling out astigmatism of the entire optical system. Furthermore, these cylindrical lenses 20 and 28 are spaced from the intermediate image planes A and A', thereby preventing noise from being produced by flaws and foreign matter.

Figure 7:
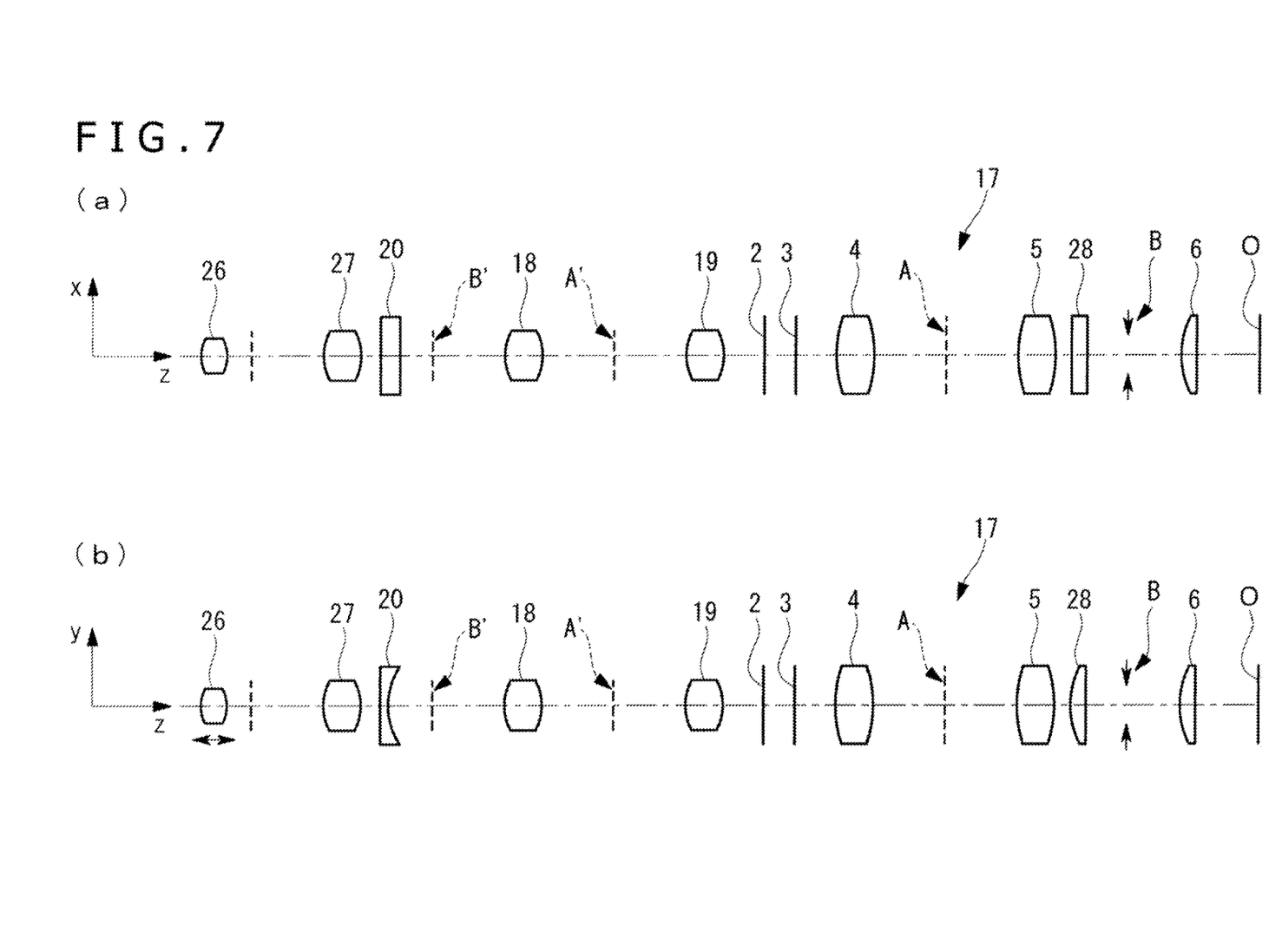
FIG. 7 is a schematic diagram of a modification of the scanning optical system of FIG. 6, illustrating a vertical cross-sectional shape thereof in (a) xz directions and in (b) yz directions.

According to the present embodiment, the two cylindrical lenses 20 and 28 are disposed in respective positions spaced from the intermediate image planes A and A' relatively closely thereto. Instead, as illustrated in FIGS. 7(a) and 7(b), large astigmatism may be generated between the two cylindrical lenses 20 and 28 by placing them in a position between the intermediate image plane A and the pupil plane B and away from the intermediate image plane A and a position that is conjugate to the above position. With this arrangement, providing the observation apparatus includes an internal focusing lens 26, even if the intermediate image plane A is greatly varied and aligned with any optical element by movement of the internal focusing lens 26, noise is prevented from being produced by flaws and foreign matter on that optical element. The reference numeral 27 in FIGS. 7(a) and 7(b) denotes a relay lens.

Figure 8:
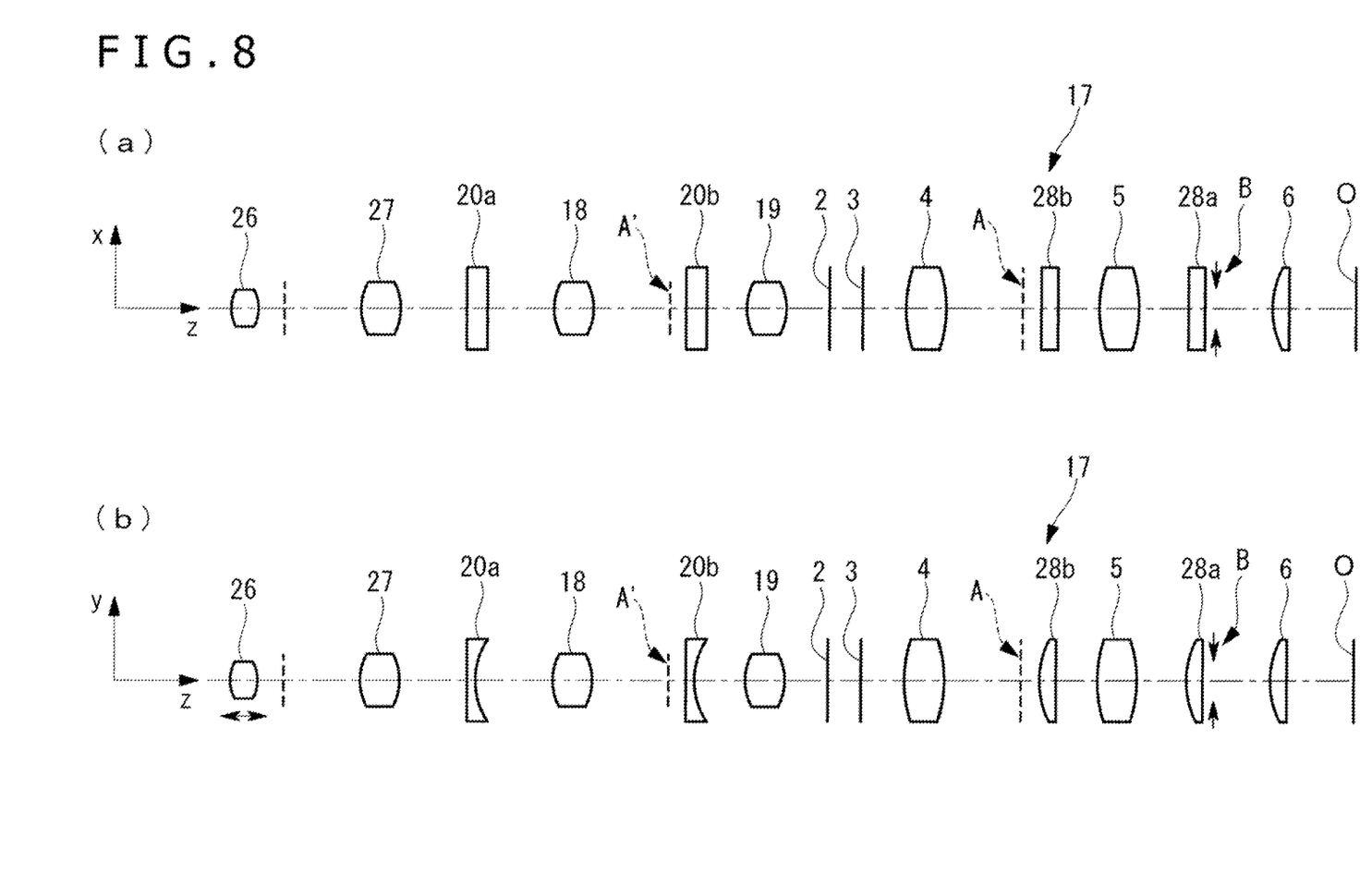
FIG. 8 is a schematic diagram of another modification of the scanning optical system of FIG. 6, illustrating a vertical cross-sectional shape thereof in (a) xz directions and in (b) yz directions.

According to the present embodiment, as illustrated in FIGS. 8(a) and 8(b), a cylindrical lens or first optical element portion or first optical element 28a may be disposed in close proximity to the pupil plane B of the objective lens 6, a cylindrical lens or first optical element portion or first optical element 28b may be disposed at a spaced interval from the cylindrical lens 28a in an optical axis S direction, and other cylindrical lenses or second optical element portions or second optical elements 20a and 20b that are complementary in shape to the cylindrical lenses 28a and 28b may be disposed in respective positions that are optically conjugate to the cylindrical lenses 28a and 28b across the intermediate image plane A, the galvanometer mirror 3, and the galvanometer mirror 2.

In this case, the cylindrical lenses 28a and 28b have positive optical powers, and the cylindrical lenses 20a and 20b have negative optical powers. The cylindrical lenses 20b and 28b are disposed respective positions in close proximity to the intermediate image planes A and A' and shifted in either of the directions along the optical axis S.

According to the present embodiment, since the cylindrical lens 28a and the cylindrical lens 20a are in conjugate positions and complementary in shape, and the cylindrical lens 28b and the cylindrical lens 20b are in conjugate positions and complementary in shape, the signs of the optical powers of the cylindrical lenses 20a and 28a may be switched around, so that the cylindrical lens 20a may have a positive optical power and the cylindrical lens 28a may have a negative optical power.

A scanning optical system 21 according to a fifth embodiment of the present disclosure will be described hereinafter with reference to the drawings.

Those parts of the present embodiment which share common structures with those of the scanning optical system 17 according to the fourth embodiment described hereinbefore are denoted by identical reference numerals and will not be described hereinafter.

Figure 9:
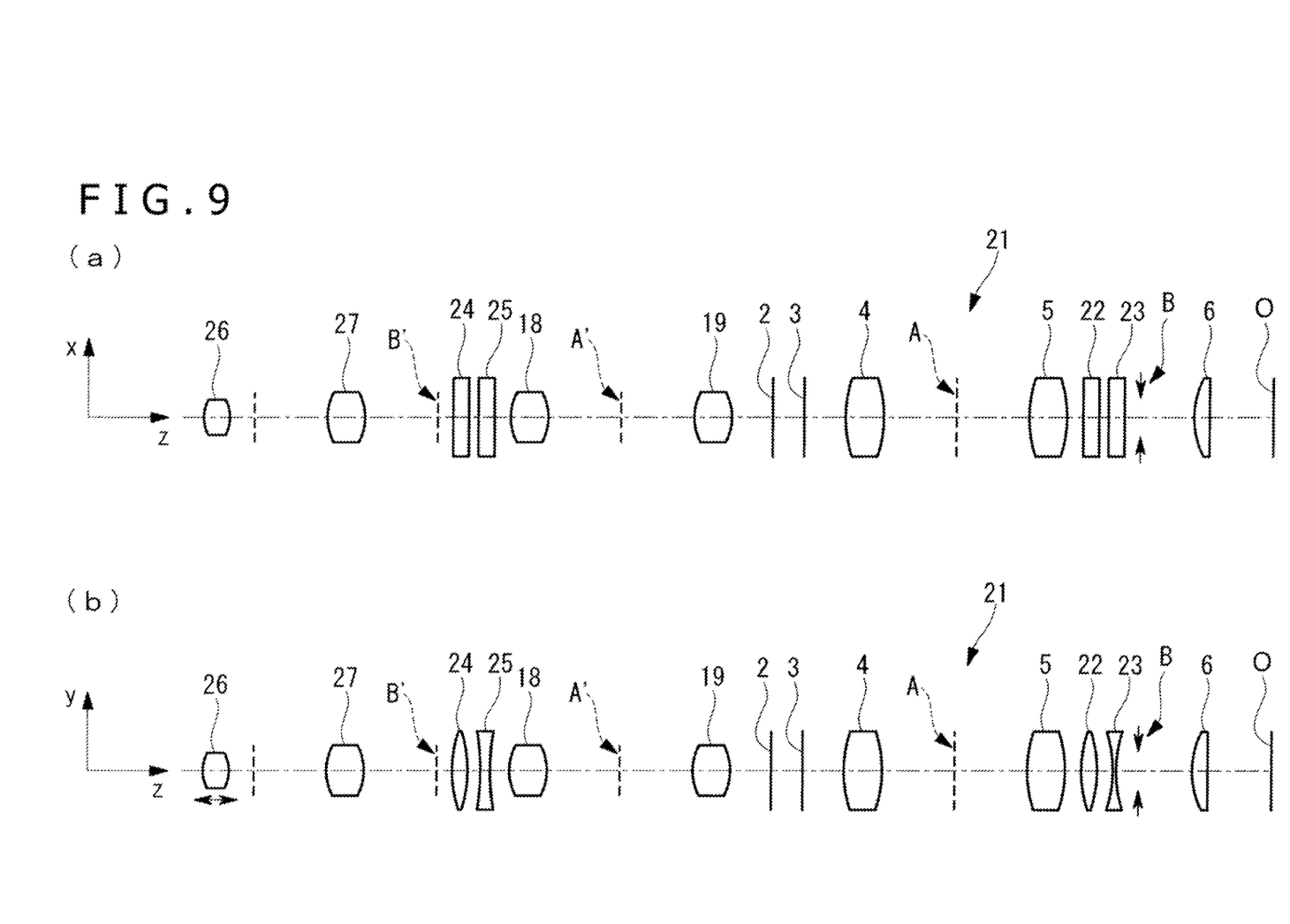
FIG. 9 is a schematic diagram of a scanning optical system according to a fifth embodiment of the present invention, illustrating a vertical cross-sectional shape thereof in (a) xz directions and in (b) yz directions.

As illustrated in FIGS. 9(a) and 9(b), the scanning optical system 21 according to the present embodiment is different from the scanning optical system 17 according to the fourth embodiment as to the layout and structures of cylindrical lenses 22, 23, 24, and 25.

According to the present embodiment, two cylindrical lenses or optical elements 22 and 23 having double convex and double concave vertical cross-sectional shapes, respectively, in the y direction are disposed in juxtaposition in place of the single cylindrical lens 28 disposed in close proximity to the pupil plane B of the objective lens 6 in the modification of the fourth embodiment illustrated in FIGS.

7(*a*) and 7(*b*), making up a first optical element of a retrofocus system having a negative optical power. Furthermore, two cylindrical lenses or optical elements 24 and 25 having double convex and double concave vertical cross-sectional shapes, respectively, in the y direction are disposed in juxtaposition in place of the cylindrical lens 20, in close proximity to the position B' that is optically conjugate to the pupil plane B of the objective lens 6, making up a second optical element of a retrofocus system having a positive optical power. The first optical elements 22 and 23 having a negative power and the second optical elements 24 and 25 having a positive power have properties complementary to each other.

The retrofocus system can have an increased distance between principal points. Using such a feature, the y-direction galvanometer mirror 3 that is shifted from the position that is optically conjugate to the pupil plane B of the objective lens 6 can be disposed in a positional relationship that is optically conjugate to the pupil plane B. By constructing both the first optical elements 22 and 23 and the second optical elements 24 and 25 as retrofocus systems according to the present embodiment, the elements from the light source to the objective lens 6 can be placed fully in a pupil conjugate relationship.

According to the present embodiment, large astigmatism can also be generated between the two groups of cylindrical lenses 22, 23, 24, and 25 by placing them in a position between the intermediate image plane A and the pupil plane B and away from the intermediate image plane A and a position that is conjugate to the above position. With this arrangement, providing the observation apparatus includes an internal focusing lens 26, even if the intermediate image plane A is greatly varied and aligned with any optical element, noise is prevented from being produced by flaws and foreign matter on that optical element.

According to the present embodiment, moreover, the cylindrical lenses 22 and 23 having a negative combined power are disposed on the pupil plane B side and the cylindrical lenses 24 and 25 having a positive combined power are disposed on the position B' side as the two groups of cylindrical lenses 22, 23, 24, and 25. Instead, the cylindrical lenses 24 and 25 having a positive combined power may be disposed on the pupil plane B side and the cylindrical lenses 22 and 23 having a negative combined power may be disposed on the position B' side.

Figure 10:
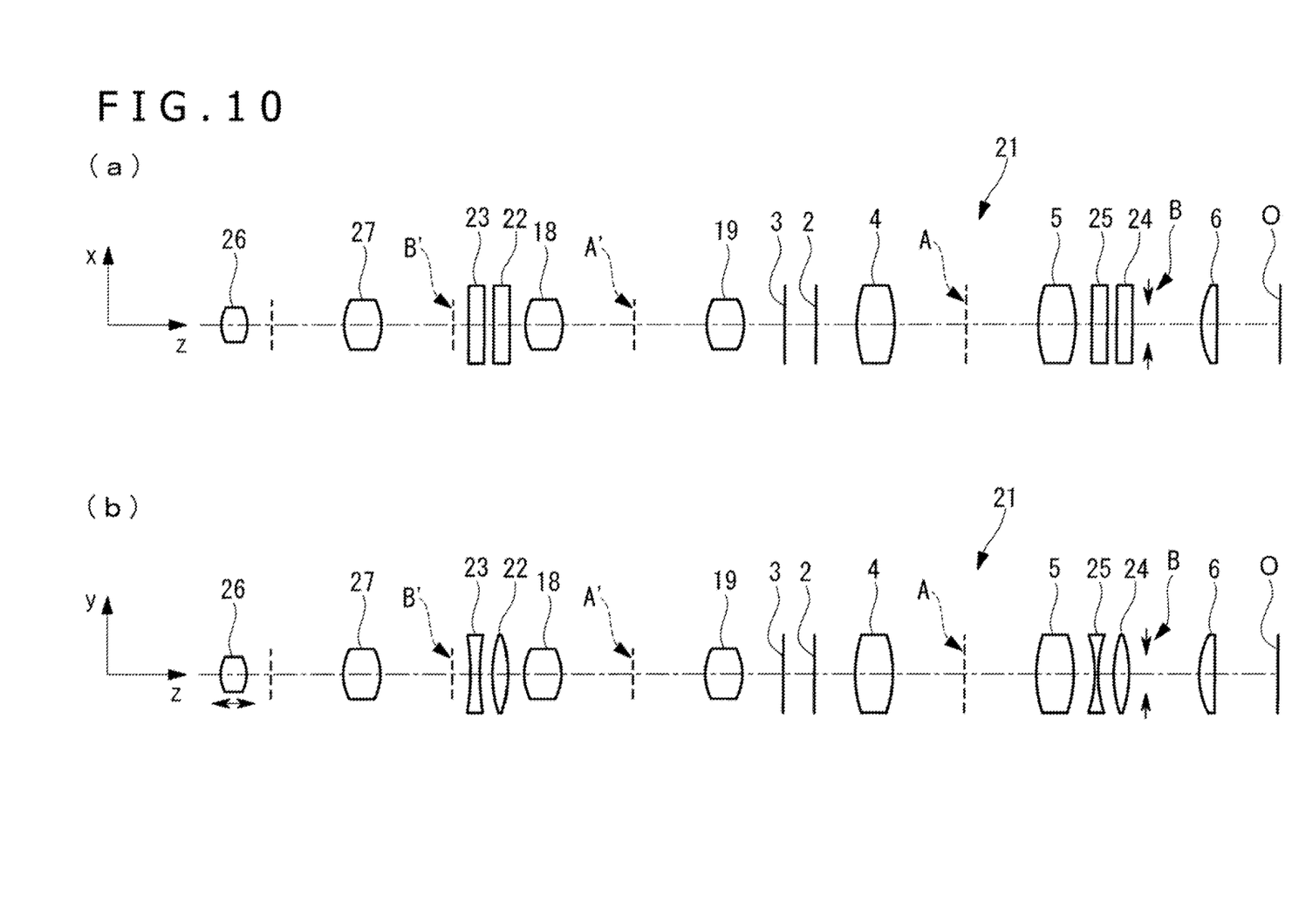
FIG. 10 is a schematic diagram of a modification of the scanning optical system of FIG. 9, illustrating a vertical cross-sectional shape thereof in (a) xz directions and in (b) yz directions.

In such a case, as shown in FIGS. 10(*a*) and 10(*b*), in the x direction where there is no optical power, the x-direction galvanometer mirror 2, the pupil plane B, and the position B' are disposed in optically conjugate positions. In the y direction, the y-direction galvanometer mirror 3, the pupil plane B, and the position B' are adjusted to optically conjugate positions using the distances between the principal points of the two groups of cylindrical lenses 22, 23, 24, and 25.

Specifically, the conjugate plane in the y direction of the position B' is moved more closely to the light source than the x-direction galvanometer mirror 2 by the cylindrical lenses 22 and 23, making the position B' and the y-direction galvanometer mirror 3 optically conjugate to each other. Moreover, the conjugate plane in the y direction of the y-direction galvanometer mirror 3 is moved more closely to the objective lens 6 than the original conjugate plane by the cylindrical lenses 24 and 25, making the y-direction galvanometer mirror 3 and the pupil plane B optically conjugate to each other.

In the present embodiment, the optical system using the internal focusing lens 26 is illustrated as the scanning system 21. However, a wavefront modulating device may be used in place of the internal focusing lens 26.

The wavefront modulating device may be a liquid crystal on silicon (LCOS) device, a variable shape device or deformable mirror, a variable shape lens, a KTN crystal, or the like, and may be disposed in close proximity to the position B'.

In sum, the disclosed technology is directed to a scanning optical system comprises two one-dimensional scanning means disposed with respect to one another at a spaced interval therebetween in an optical axis direction for scanning a light beam from a light source in two scanning directions. An objective lens is configured to focus the light beam scanned by the scanning means onto a target. A plurality of optical elements is disposed in positions spaced from an intermediate image plane in the optical axis direction and having different optical powers in the two scanning directions. The positions and the optical powers of the respective optical elements are set to compensate for the spaced interval between the two scanning means in the optical axis direction.

The plurality of optical elements are disposed at a spaced interval therebetween across the intermediate image plane in the optical axis direction. The plurality of optical elements is defined by two optical elements disposed on one side of the intermediate image plane at a spaced interval therebetween in the optical axis direction. One of the plurality of optical elements that is closer to the intermediate image plane and another one of the plurality of optical elements that is farther from the intermediate image plane have respective optical powers of different signs. The optical elements have different combined optical powers in the two scanning directions. The plurality of optical elements make up an afocal optical system and are disposed between the scanning means and a pupil plane of the objective lens. The plurality of optical elements include a first optical element portion disposed between the scanning means and a pupil plane of the objective lens and a second optical element portion disposed in a position that is optically conjugate to the first optical element portion having a property optically complementary to the first optical element portion, and canceling out an optical power of the first optical element portion in an entire optical system.

The first optical element portion includes respective third and fourth optical elements disposed closely to the pupil plane of the objective lens at a spaced interval therebetween in the optical axis direction. The third optical element that is closer to the pupil plane and the fourth optical element that is farther from the pupil plane have respective optical powers of different signs. The first optical element portion includes two first optical elements, one of the first optical elements is disposed closely to the pupil plane of the objective lens and other first optical element is disposed at a spaced interval from the pupil plane of the objective lens in the optical axis direction. The second optical element portion includes two second optical elements. The second optical elements are disposed in respective positions that are optically conjugate to the first optical elements of the first optical element portion and having respective properties that are optically complementary to each other.

Another aspect of the disclosed technology is directed to an observation apparatus having a scanning optical system that comprises two one-dimensional galvanometer mirrors disposed with respect to one another at a spaced interval therebetween in an optical axis direction for scanning a light beam from a light source in two scanning directions. An objective lens is configured to focus the light beam scanned by the galvanometer mirrors onto a target. The observation apparatus further comprises an internal focusing lens. A plurality of optical elements is disposed in positions spaced from an intermediate image plane in the optical axis direction and having different optical powers in the two scanning directions. The positions and the optical powers of the respective plurality of optical elements are set to compensate for the spaced interval between the two one-dimensional galvanometer mirrors in the optical axis direction.

A further aspect of the disclosed technology is directed to a scanning optical system comprises a first one-dimensional scanner configured to scan a light beam from a light source in a first direction. A second one-dimensional scanner is disposed at a spaced interval from the first one-dimensional scanner in the optical axis direction and configured to scan the light beam in a second direction. A first relay lens is configured to relay the light beam scanned by the first one-dimensional scanner and the second one-dimensional scanner and is configured to form an intermediate image at a position on the intermediate image plane. A second relay lens is configured to relay the light beam relayed by the first relay lens. An objective lens is configured to focus the light beam relayed by the second relay lens onto a target. A first optical element is disposed in a first position spaced from the intermediate image plane in the optical axis direction and having a first optical power different in the first direction and the second direction. A second optical element is disposed in a second position spaced from the intermediate image plane in the optical axis direction and having a second optical power different in the first direction and the second direction. The first position, the second position, the first optical power and the second optical power are set to compensate for the spaced interval between the first one-dimensional scanner and the second one-dimensional scanner in the optical axis direction.

The first optical element is disposed between the first relay lens and the intermediate image plane. The second optical element is disposed between the second relay lens and the intermediate image plane. The first optical element is disposed between the second relay lens and the intermediate image plane. The second optical element is disposed between the second relay lens and the intermediate image plane. The first optical element has no power in a first cross sectional plane defined by the optical axis direction and the first direction. The first optical element has positive power in a second cross sectional plane defined by the optical axis direction and the second direction. The second optical element has no power in the first cross sectional plane and the second optical element has negative power in the second cross sectional plane. The first optical element is disposed between the second relay lens and the objective lens. The second optical element is disposed between the second relay lens and the objective lens. The scanning optical system further comprises a third relay lens and a fourth relay lens disposed between the first relay lens and the third relay lens. The first optical element is disposed between the third relay lens and the fourth relay lens. The second optical element is disposed between the intermediate image plane and the second relay lens. The scanning optical system further comprises a third relay lens and a fourth relay lens disposed between the first relay lens and the third relay lens. A fifth relay lens is disposed between the first relay lens and the fourth relay lens. The first optical element is disposed between the third relay lens and the fourth relay lens and the second optical element is disposed between the second relay lens and the objective lens.

The scanning optical system further comprises a third relay lens a fourth relay lens disposed between the first relay lens and the third relay lens. A fifth relay lens is disposed between the first relay lens and the fourth relay lens. The first optical element includes a first portion and a second portion. The second optical element includes a third portion and a fourth portion. The first portion is disposed between the third relay lens and the fourth relay lens. The second portion is disposed between the fourth relay lens and the fifth relay lens. The third portion is disposed between the intermediate image plane and the second relay lens and the fourth portion is disposed between the second relay lens and the objective lens. The scanning optical system further comprises a third relay lens. A fourth relay lens is disposed between the first relay lens and the third relay lens. A fifth relay lens is disposed between the first relay lens and the fourth relay lens. The first optical element includes a first portion and a second portion. The second optical element includes a third portion and a fourth portion. The first portion is disposed between the third relay lens and the fourth relay lens. The second portion is disposed between the third relay lens and the fourth relay lens. The third portion is disposed between the second relay lens and the objective lens. The fourth portion is disposed between the second relay lens and the objective lens.

The present disclosure is similar to the disclosure disclosed in JP 2011-224037A in that it uses retrofocus cylindrical lenses. However, the present disclosure is different from the above prior example in that the distances between the principal points in the retrofocus system are positively used to make proximity galvanometer mirrors pupil conjugate.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof;

the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

REFERENCE NUMERALS LIST 1, 11, 14, 17, 21 Scanning optical system
2, 3 Galvanometer mirror or scanning means
6 Objective lens
7, 8, 12, 13, 15, 16, 20, 20a, 20b, 22, 23, 24, 25, 28, 28a, 28b Cylindrical lens or optical element or first optical element or second optical element or first optical element portion or second optical element portion
26 Internal focusing lens
A Intermediate image plane
B Pupil plane
O Object or target
S Optical axis

What is claimed is:

1. A scanning optical system comprising:
two one-dimensional scanning mirrors disposed with respect to one another at a spaced interval therebetween in an optical axis direction for scanning a light beam from a light source in two scanning directions;
an objective lens configured to focus the light beam scanned by the scanning mirrors onto a target; and
a plurality of optical elements disposed in positions spaced from an intermediate image plane in the optical axis direction and having different optical powers in the two scanning directions,
wherein the positions and the optical powers of the respective optical elements are set to compensate for the spaced interval between the two scanning mirrors in the optical axis direction,
the plurality of optical elements are disposed at a spaced interval therebetween across the intermediate image plane in the optical axis direction; and
the optical elements have different combined optical powers in the two scanning directions.

2. An observation apparatus comprising the scanning optical system according to claim 1.

3. The observation apparatus of claim 2 further comprising an internal focusing lens.

4. A scanning optical system comprising:
two one-dimensional scanning mirrors disposed with respect to one another at a spaced interval therebetween in an optical axis direction for scanning a light beam from a light source in two scanning directions;
an objective lens configured to focus the light beam scanned by the scanning mirrors onto a target; and
a plurality of optical elements disposed in positions spaced from an intermediate image plane in the optical axis direction and having different optical powers in the two scanning directions,
wherein the positions and the optical powers of the respective optical elements are set to compensate for the spaced interval between the two scanning mirrors in the optical axis direction,
the plurality of optical elements is defined by two optical elements disposed on one side of the intermediate image plane at a spaced interval therebetween in the optical axis direction; and
one of the plurality of optical elements that is closer to the intermediate image plane and another one of the plurality of optical elements that is farther from the intermediate image plane have respective optical powers of different signs.

5. An observation apparatus comprising the scanning optical system according to claim 4.

6. The observation apparatus of claim 5 further comprising an internal focusing lens.

* * * * *